United States Patent
Lif et al.

(10) Patent No.: US 7,053,247 B2
(45) Date of Patent: May 30, 2006

(54) PROCESS FOR THE MANUFACTURE OF DIETHYLENETRIAMINE AND HIGHER POLYETHYLENEPOLYAMINES

(75) Inventors: Johan Lif, Skärhamn (SE); Kristina Ekenberg, Stora Höga (SE)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/484,323

(22) PCT Filed: Jul. 5, 2002

(86) PCT No.: PCT/SE02/01351

§ 371 (c)(1),
(2), (4) Date: Jan. 21, 2004

(87) PCT Pub. No.: WO03/010125

PCT Pub. Date: Feb. 6, 2003

(65) Prior Publication Data

US 2004/0171884 A1  Sep. 2, 2004

(30) Foreign Application Priority Data

Jul. 24, 2001 (SE) .................................. 0102590

(51) Int. Cl.
*C07C 209/60* (2006.01)
(52) U.S. Cl. .................................... 564/470
(58) Field of Classification Search ................ 564/470
See application file for complete search history.

(56) References Cited

U.S. PATENT DOCUMENTS

| | | | |
|---|---|---|---|
| 4,568,746 A | 2/1986 | Cowherd, III | 544/358 |
| 4,956,328 A | 9/1990 | Frohning et al. | 502/242 |
| 5,243,078 A * | 9/1993 | Agrawal et al. | 564/470 |
| 5,410,086 A | 4/1995 | Burgess | 564/470 |
| 5,952,529 A | 9/1999 | Chang et al. | 564/480 |
| 5,958,825 A | 9/1999 | Wulff-Döring et al. | 502/300 |
| 5,994,585 A * | 11/1999 | Gunther-Hanssen | 564/480 |

FOREIGN PATENT DOCUMENTS

| | | |
|---|---|---|
| GB | 1 508 460 | 4/1978 |
| WO | WO 01/66247 A2 | 9/2001 |

OTHER PUBLICATIONS

International Preliminary Examination Report of International Application No. PCT/SE02/01351, dated Jun. 12, 2003.
Twigg et al., "Effects of alumina incorporation in coprecipitated NiO—$Al_2O_3$ catalysts," Applied Catalysts A: General 190 (2000) pp. 61-72.
Kiš, et al., "Structural and textural properties of the NiO—$Al_2O_3$ catalyst," Polyhedron, vol. 17, No. 1, (1998), pp. 27-34.
Balker et al., "Synthesis of W-Phenylalkyldimethylamines from Corresponding Alcohols," Synthetic Communications, vol. 8, No. 1 (1978), pp. 27-32.

* cited by examiner

*Primary Examiner*—Brian Davis
(74) *Attorney, Agent, or Firm*—Michelle J. Burke; Ralph J. Mancini

(57) ABSTRACT

The invention relates to a process for the manufacture of diethylenetriamine and higher polyethylenepolyamines by a transamination of ethylenediamine. The transamination is performed at a temperature from 135° C. to 180° C. at a pressure from 5 Mpa to 40 Mpa in the presence of hydrogen and a particulate catalysts containing 26 to 65% by weight of nickel on an oxide carrier. A high conversion degree of ethylenediamine and a high selectivity to form acyclic polyethylenepolyamines, such as diethylenetriamine are obtained by the process. The formation of cyclic amine compounds, e.g. piperazine, is low.

11 Claims, No Drawings

PROCESS FOR THE MANUFACTURE OF DIETHYLENETRIAMINE AND HIGHER POLYETHYLENEPOLYAMINES

This application claims priority of PCT Application No. PCT/SE02/01351filed Jul. 5, 2002, and Swedish Patent Application No. 0102590-7, filed Jul. 24, 2001.

The invention relates to a process for the manufacture of diethylenetriamine and higher polyethylenepolyamines by transamination of ethylenediamine. The process exhibits a high conversion rate of ethylenediamine and a high selectivity to form acyclic polyethylenepolyamines, such as diethylenetriamine. The formation of cyclic amine compounds, e.g. piperazine, is low.

The most desirable products in the manufacture of ethylene amines are acyclic, preferably linear, ethylene amines containing primary and secondary amino groups. Ethylene amines containing heterocyclic rings are of less commercial interest. Thus, U.S. Pat. No. 4,568,746 discloses a process for the production of an amine composition containing a high proportion of diethylenetriamine to piperazine, by transamination of ethylenediamine in the presence of a nickel, cobalt or rhodium catalyst at temperatures between 170° C. and 210° C. and at a pressure of 1000 psig. Specifically disclosed catalysts are Raney nickel and Raney cobalt catalysts having a particle size of 20–60 μm, Rh supported on alumina, Ni/Re/B supported on silica and Ni/Zr supported on kieselguhr. The Raney nickel or Raney cobalt catalyst is unsuitable to use, since they are brittle and difficult to handle. In addition, the small particle size of the Raney nickel or the Raney cobalt catalyst makes the catalyst inexpedient to use in continuous methods as well as difficult to remove from the reaction mixture. On the other hand, the catalysts having a support give a comparatively high yield of piperazine.

The U.S. Pat. No. 5,410,086 also describes a method of controlling the ratio of diethylenetriamine to piperazine, when transaminating ethylenediamine in the presence of hydrogen and a hydrogenation catalyst, by adjusting the hydrogen concentration in the liquid reaction phase. Preferred hydrogenation catalysts are Raney nickel and Raney cobalt or a nickel/rhenium/boron catalyst.

The working examples disclose a transamination process of ethylenediamine, where the reaction is performed in a tube reactor which has been loaded with a catalyst containing 6.2 weight percent nickel, 4.4 weight percent rhenium and 1.8 weight percent boron on a support.

Further, the publication GB 1 508 460 describes a process for the manufacture of diethylenetriamine by transamination of ethyleneamine in the presence of a catalyst containing at least one transition metal of group 8 of the Periodic Table of the Elements at a temperature from 100° C. to 150° C., the reaction being taken to a degree of conversion of 70% or less. Preferably the catalyst occupies at least 20% by volume of the reaction zone, and the reaction time is from 5 to 10 hours.

The general problem in these transamination processes of ethylenediamine to diethylenetriamine and higher polyethylenepolyamines is the fact that they at moderate temperatures and pressures result in too high a proportion of cyclic ethyleneamine compounds, such as piperazine, and/or that the conversion degree of ethylenediamine is too low. Thus, there is a need for improvements leading to a high conversion degree of ethylenediamine and at the same time to a favourable ratio between the desired acyclic polyethylenepolyamines and the cyclic polyethylenepolyamines at favourable reaction conditions.

It has now been found that said objectives can be achieved by performing the transamination process under mild reaction conditions in the presence of a catalyst containing a high amount of metallic nickel on a porous oxide support. According to the present invention diethylenetriamine and higher acyclic polyethylenepolyamines are manufactured by transamination of ethylenediamine at a temperature of 135–180° C., preferably 150–165° C., at a pressure from 5 MPa to 40 MPa, preferably from 8–35 MPa, and in the presence of hydrogen and a particulate catalyst containing 26–65%, preferably 30–65%, by weight of metallic nickel on a porous oxide support, preferably containing alumina, silica or a mixture thereof. Said transamination can be performed batchwise but a continuous process is preferred. At a temperature from 145° C. to 165° C. and a conversion degree of 4 to 30% of ethylenediamine, high selectivities for acyclic polyethylenepolyamines can be obtained. Thus, at a conversion degree of 10%, the reaction mixture may have a weight ratio between acyclic polyethylenepolyamine compounds and cyclic ethyleneamines of above 20:1 and for 15% conversion degree of above 15:1. The corresponding ratios obtained in the working examples of the U.S. Pat. No. 5,410,086 are essentially lower.

The catalytical active part of the catalyst of the present invention comprises a large amount of metallic nickel deposited on a porous oxide support. The catalyst may also contain supplementary, catalytical effective metals commonly used in amination processes, such as cobalt, iron, copper, palladium, or mixtures thereof. Said metals may be present in a total metallic amount of 0,1% to 12% by weight of the amount of metallic nickel. Nickel and any supplementary metals are mainly responsible for the catalytic transamination effect.

The catalytic effect may also be promoted by the presence of a minor amount of another metal to achieve e.g. improved selectivity for the desired products. These promoters may be present in a total metallic amount of 0.1% to 15% by weight of the amount of metallic nickel. Examples of suitable promoters are calcium, magnesium, strontium, lithium, sodium, potassium, barium, cesium, tungsten, iron, ruthenium, zinc, uranium, titanium, rhodium, palladium, platinum, iridium, osmium, silver, gold, molybdenum, rhenium, cadmium, lead, rubidium, boron and manganese. Thus, for example rhenium has a pronounced positive effect on both the selectivity and the conversion degree, while ruthenium has a tendency to decrease the conversion degree but a strong selectivity for the formation of acyclic polyethylenepolyamines.

Examples of suitable porous oxide supports are silica or various forms of alumina, for example alfa, delta, theta or gammaforms or mixtures thereof. Preferably the content of alumina is at least 25% by weight of the support. The support may also contain minor amounts of other oxidic materials, such as titania, magnesia and zirconia. Especially preferred are alumina or combinations between alumina and silica containing at least 25% by weight of alumina. The inner surface area of the support may vary from 20 to 1000, preferably from 40 to 400, square meters per gram support. The support normally constitutes between 30% and 74% by weight of the whole catalyst. In a preferred embodiment of the invention the transamination catalyst contains nickel promoted with ruthenium, rhenium, palladium or platinum on a porous support containing alumina or a combination of alumina and silica. The catalytic active area of the catalyst is suitably from 10 to 70 square meters per gram of catalyst. Normally, the catalyst has such a particle size that at least 80%, preferably at least 95%, by weight, have a size between 0.1 and 10 mm, preferably between 0.2 and 5 mm.

The transamination catalyst may be prepared by first coprecipitating a nickel salt and salts of any supplementary and/or promoting metals, for instance a nitrate salt, on a granulated support according to the invention, in an alkaline solution or by impregnating the granulated support with the metal salts. Besides the nitrate salts the most commonly used metal salts are acetate, acetylacetonate, ammoniumsulphate, borate, bromide, carbonate, chloride, chromite, citrate, cyanide, 2-ethylhexanoate, fluoride, formate, hydroxide, hydroxyacetate, iodide, methoxide, 2-methoxyethoxide, nitrocylchloride, nitrocylnitrate, octanoate, oxalate, perchlorate, phosphate, sulfamate, sulphate and tetrafluoroborate. The precipitate and impregnate are suitably washed with deionized water and pressed in molds or extruded. The granules obtained may then be dried in air and calcined in air at a temperature in the range from 200 to 1200° C., normally 300 to 500° C., depending on the decomposition temperature of the salts used, until the salts are transferred into oxides. Finally the metal oxides are reduced to metallic form in the presence of hydrogen at a temperature from 150 to 600° C., depending on the metal oxides to be converted, until a desired degree of reduction is reached. In case the catalyst contains two or more metals, a combined precipitation and impregnation method can be used. Suitable catalyst preparation methods are further described in M. V. Twigg, J. T. Richardson, Appl. Catal. A 190 (2000) 61–72, E. Kis et al., Polyhedron 17, 1 (1998) 27–34 and A. Baiker, W. Richarz, Syn. Comm. 8(1) (1978) 27–32.

The transamination process may advantageously be performed both continuously and batch-wise. In a continuous process hydrogen and ethylenediamine are suitably passed as a gas and liquid mixture under pressure through a fixed or fluidised bed of the catalyst at the desired temperature. In case of a solid bed, at least 80%, preferably at least 95% by weight of the catalyst particles normally have a size from 0.5 mm to 10 mm, preferably from 1 mm to 5 mm. In a fluidised bed, at least 80%, preferably at least 95% by weight of the catalyst particles are from 0.1 mm to 2 mm, preferably from 0.2 to 1 mm. The reaction mixture obtained contains transaminated products, such as diethylenetriamine, triethylenetetraamine and piperazine, unreacted ethylenediamine, ammonia eliminated in the transamination reaction and hydrogen. The reaction mixture is normally worked up by first separating the low molecular weight compounds, hydrogen and ammonia, from unreacted ethylenediamine and the various transamination products, which are subjected to fractional distillation. Hydrogen and ethylenediamine are returned to the process.

The hydrogen is present in the transamination process to ensure a high yield of desired acyclic polyethylenepolyamines and to inhibit or reduce the poisoning of the catalyst. Normally, the amount of hydrogen is from 0.1 to 3 moles per mole of ethylenediamine. It is desirable to keep hydrogen and ethylenediamine to an essential part in the liquid state. Thus, the pressure in the reactor will be dependent mainly on the reaction temperature, but also on the amounts of hydrogen and ethylenediamine. Since the reaction temperature is moderate the pressure will also be moderate and suitably between 5 MPa and 40 MPa, preferably between 8 and 35 MPa, and the temperature from 135° C. to 185° C., preferably between 145° C. and 165° C. During these conditions the conversion degree of ethylenediamine is good and the selectivity for linear polyethylenepolyamines is high.

EXAMPLE

A cage containing one of the catalysts according to Table I, was placed in an autoclave equipped with a stirrer and a temperature control device. The autoclave was then flushed with nitrogen gas and charged with 120 grams of ethylenediamine. After closing the autoclave, hydrogen was introduced to a pressure of 30 bar and the reactor content temperature was increased to the reaction temperature during stirring and held at this temperature for 4 hours, whereupon the reaction was stopped by reducing the temperature. The reaction mixture obtained was analysed with respect to ethylenediamine (EDA), diethylenetriamine (DETA), higher acyclic polyethylenepolyamines (HAM) and piperazine compounds (PIP). The transamination results are shown in Table II.

TABLE I

Transamination catalysts

| Test No. | Support % by weight | Nickel % by weight | Other metals % by weight | Catalytic active area m$^2$/g | Catalyst Size mm | Catalyst Amount g |
|---|---|---|---|---|---|---|
| 1 | Alumina, 100 | 55 | — | 31 | 1.6 | 10.2 |
| 2 | Alumina, 100 | 55 | — | 31 | 1.6 | 9.1 |
| 3 | Alumina, 100 | 47 | — | 14 | 3.2 | 10.2 |
| 4 | Alumina, 100 | 47 | — | 14 | 3.2 | 10.0 |
| 5 | Alumina, 100 | 47 | — | 14 | 3.2 | 10.0 |
| 6 | Alumina, 50, silica, 50 | 60 | — | 35 | 1.2 | 10.2 |
| 7 | Alumina, 50, silica, 50 | 60 | — | 35 | 1.2 | 10.3 |
| 8 | Alumina, 50, silica, 50 | 60 | — | 35 | 1.2 | 10.1 |
| 9 | Silica, 100 | 38 | — | 32 | 1.2 | 10.2 |
| 10 | Alumina, 100 | 33 | — | 8 | 4.8 | 10.2 |
| 11 | Alumina, 100 | 33 | — | 8 | 4.8 | 10.8 |
| 12 | Alumina, 50/silica 50 | 60 | Ru 0.75[1] | >35 | 1.2 | 9.8 |
| 13 | Alumina, 50/silica 50 | 60 | Ru 0.75[1] | >35 | 1.2 | 8.7 |
| 14 | Alumina, 50/silica 50 | 60 | Ru 4.5[1] | >36 | 1.2 | 8.6 |
| 15 | Alumina, 50/silica 50 | 60 | Re 0.75[2] | >35 | 1.2 | 8.0 |
| 16 | Alumina, 50/silica, 50 | 60 | Ru 0.75[3] | >35 | 1.2 | |
| A | alumina, 100 | 16 | — | 6 | 4.8 | 7.2 |
| B | Silica, 100 | 15 | — | 10 | 3.2 | 7.4 |

[1] impregnated with ruthenium chloride
[2] impregnated with ammonium perrhenate
[3] impregnated with ruthenium nitrosylnitrate

TABLE II

Transamination results

| Test No. | Temp ° C. | Conversion % EDA | Transamination products weight % | | | Weight ratio[1] |
|---|---|---|---|---|---|---|
| | | | PIP | DETA | HAM | |
| 1 | 160 | 27.3 | 11.8 | 71.6 | 16.4 | 7.5 |
| 2 | 155 | 11.3 | 7.5 | 84.6 | 7.6 | 12.3 |
| 3 | 170 | 38.4 | 15.8 | 62.6 | 21.3 | 5.3 |
| 4 | 162 | 20.4 | 9.1 | 78.6 | 12.0 | 10.0 |
| 5 | 160 | 15.0 | 4.9 | 87.7 | 7.2 | 19.5 |
| 6 | 150 | 9.1 | 3.9 | 92.1 | 3.7 | 24.3 |
| 7 | 152 | 15.1 | 6.0 | 86.7 | 7.1 | 15.6 |
| 8 | 160 | 38.0 | 15.1 | 65.1 | 19.6 | 5.6 |

TABLE II-continued

Transamination results

| Test No. | Temp ° C. | Conversion % EDA | Transamination products weight % | | | Weight ratio[1] |
|---|---|---|---|---|---|---|
| | | | PIP | DETA | HAM | |
| 9 | 170 | 23.8 | 16.0 | 59.6 | 24.1 | 5.2 |
| 10 | 170 | 52.3 | 20.6 | 25.9 | 53.2 | 3.8 |
| 11 | 150 | 13.8 | 12.1 | 63.1 | 24.5 | 7.3 |
| 12 | 170 | 42.7 | 14.5 | 63.3 | 21.8 | 5.9 |
| 13 | 150 | 5.4 | 2.2 | 95.9 | 1.1 | 44.5 |
| 14 | 150 | 3.5 | 1.5 | 97.3 | 0.0 | 64.1 |
| 15 | 150 | 15.4 | 5.8 | 84.3 | 14.5 | 16.1 |
| 16 | 150 | 11.2 | 4.0 | 89.2 | 6.3 | 23.6 |
| A | 170 | 5.5 | 32.8 | 58 | 8.3 | 2.0 |
| B | 170 | 2.8 | 28.5 | 66.4 | 3.7 | 2.5 |

[1])DETA + HAM/PIP

From the results it is evident that the catalyst according to the invention has a high activity already at 150° C. At temperatures about 150–165° C. the catalysts according to the invention have high selectivities to the formation of diethylenetriamine and polyethylenepolyamines as well as a satisfactory conversion degree. The presence of ruthenium improves the selectivity further, while rhenium increases both the selectivity and the conversion degree. The low temperature also reduces the pressure where hydrogen is present in liquid form. The test A and B are comparison tests and show an unfavourable combination of low conversion degree and low selectivity for the formation of acyclic compounds.

The invention claimed is:

1. A process for the manufacture of diethylenetriamine and higher linear polyethylenepolyamines by a transamination reaction of ethylenediamine wherein the reaction is performed at a temperature from about 135° C. to about 180° C., at a pressure from about 5 MPa to about 40 Mpa, and in the presence of hydrogen and a particulate catalyst comprising 26 to about 65% by weight of metallic nickel on an porous oxide support.

2. A process according to claim 1 wherein the reaction temperature is from 145° C. to 165° C.

3. A process according to claim 1 wherein the porous oxide support contains alumina, silica or a mixture thereof, and the particulate catalyst comprises about 30 to about 65% by weight of metallic nickel.

4. A process according to claim 3 wherein the porous oxide support is alumina or a mixture of alumina and silica comprising at least 25% by weight of alumina.

5. A process according to claim 1 wherein the catalyst has a particle size such that at least 80% by weight of the particles have a size from about 0.1 mm to about 10 mm.

6. A process according to claim 1 wherein the catalyst further comprises, in metallic form, cobalt, iron, copper, palladium or a mixture thereof in a total amount of about 0.1% to about 12% by weight of the amount of metallic nickel.

7. A process according to claim 1 wherein the catalyst further comprises a metal selected from the group consisting of calcium, magnesium, strontium, lithium, sodium, potassium, barium, cesium, tungsten, iron, ruthenium, zinc, uranium, titanium, rhodium, palladium, platinum, iridium, osmium, silver, gold, molybdenum, rhenium, cadmium, lead, rubidium, boron, manganese or a mixture thereof in a total metallic amount of about 0.1 to about 15% by weight of the amount of metallic nickel.

8. A process accordIng to claim 7 wherein the metal is rhenium, ruthenium, palladium or platinum.

9. A process according to claim 1 wherein the process is a continuous process.

10. A process according to claim 9 wherein the amination reaction is performed in a tubular reactor having a fixed bed.

11. The process of claim 1 wherein said higher linear polyethylenepolyamine is diethylenetriamine.

* * * * *